United States Patent
Dong

(10) Patent No.: US 9,161,726 B2
(45) Date of Patent: Oct. 20, 2015

(54) IMAGING SYSTEM SUBJECT SUPPORT MOTION ALGORITHM(S)

(75) Inventor: Shufang Dong, Mayfield Heights, OH (US)

(73) Assignee: Koninklijke Philips N.V., Eindhoven (NL)

( * ) Notice: Subject to any disclaimer, the term of this patent is extended or adjusted under 35 U.S.C. 154(b) by 183 days.

(21) Appl. No.: 13/984,858

(22) PCT Filed: Feb. 16, 2012

(86) PCT No.: PCT/IB2012/050723
§ 371 (c)(1),
(2), (4) Date: Aug. 12, 2013

(87) PCT Pub. No.: WO2012/110982
PCT Pub. Date: Aug. 23, 2012

(65) Prior Publication Data
US 2013/0315381 A1    Nov. 28, 2013

Related U.S. Application Data

(60) Provisional application No. 61/444,155, filed on Feb. 18, 2011.

(51) Int. Cl.
*A61B 6/04* (2006.01)
*A61B 6/03* (2006.01)

(52) U.S. Cl.
CPC .............. *A61B 6/0407* (2013.01); *A61B 6/035* (2013.01); *A61B 6/0457* (2013.01)

(58) Field of Classification Search
CPC ...... A61B 6/027; A61B 6/032; A61B 6/0407; A61B 6/0457; A61B 6/4441; A61B 6/035; A61N 5/1037

USPC ................................ 378/15, 17, 20, 208, 209
See application file for complete search history.

(56) References Cited

U.S. PATENT DOCUMENTS

| | | |
|---|---|---|
| 4,789,929 A | 12/1988 | Nishimura et al. |
| 5,598,453 A | 1/1997 | Baba et al. |
| 5,832,056 A | 11/1998 | Mochitate et al. |
| 6,381,299 B1 | 4/2002 | Baba et al. |
| 7,313,216 B2 | 12/2007 | Nishide et al. |

(Continued)

FOREIGN PATENT DOCUMENTS

| | | |
|---|---|---|
| EP | 0405862 A1 | 1/1991 |
| WO | 2006113323 A2 | 10/2006 |
| WO | 2010128417 A1 | 11/2010 |

OTHER PUBLICATIONS

Arevalo, Sinusoidal Velocity Profiles for Motion Control, Apr. 2001, ASPE Proceedings, Control of Precision Systems, p. 1-4.*
Bowling, Advances in Motion Profiling, Dec. 2008, PhD Dissertation, University of New Mexico, p. 26, 27, 156, 159, 161, 162.*
Li et al., Motion profile planning for reduced jerk and vibration residuals, Mar. 2007, SIMTech technical reports, vol. 8, No. 1, p. 32, 33, 36.*

(Continued)

*Primary Examiner* — Irakli Kiknadze
*Assistant Examiner* — Julio M Duarte-Carvajalino

(57) ABSTRACT

An imaging system (400) includes a subject support (412) configured to carry a subject being imaged in an examination region of the imaging system and a subject support controller (418) that positions the subject support and hence the subject in the examination region for scanning the subject based on a motion algorithm which reduces subject support vibration during scanning relative to a trapezoidal or s-curve motion algorithm, for a given translation duration and a given translation distance.

21 Claims, 13 Drawing Sheets

(56) References Cited

U.S. PATENT DOCUMENTS

| | | |
|---|---|---|
| 2006/0034419 A1 | 2/2006 | Nishide et al. |
| 2007/0211845 A1* | 9/2007 | Nishide et al. .................... 378/4 |
| 2008/0013674 A1 | 1/2008 | Zhang et al. |
| 2008/0031407 A1 | 2/2008 | Satta et al. |
| 2009/0252300 A1* | 10/2009 | Schwartz et al. ............. 378/209 |
| 2010/0134315 A1 | 6/2010 | Teders et al. |
| 2010/0166138 A1 | 7/2010 | Yan |
| 2010/0310040 A1 | 12/2010 | Hsieh et al. |

OTHER PUBLICATIONS

Bohlke, Using Input Shaping to Minimize Residual Vibration in Flexible Space Structures, Jun. 1995, MSc Dissertation, Massachusetts Institute of Technology, p. 17, 19.*

Altintas et al., Machine tool feed drives, Jun. 2011, CIRP Annals—Manufacturing Technology, p. 779, 780, 791, 792.*

Zhou, L., et al.; Modeling of stepper motor control system and running curve simulation; 2011; Electric Machines and Control; 15(1)20-25.

* cited by examiner

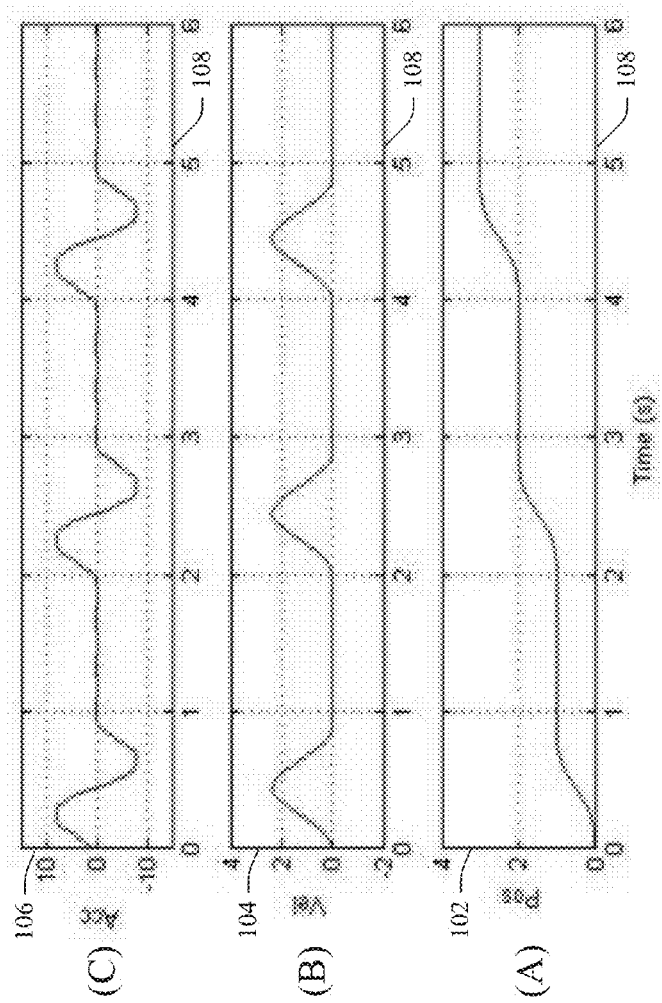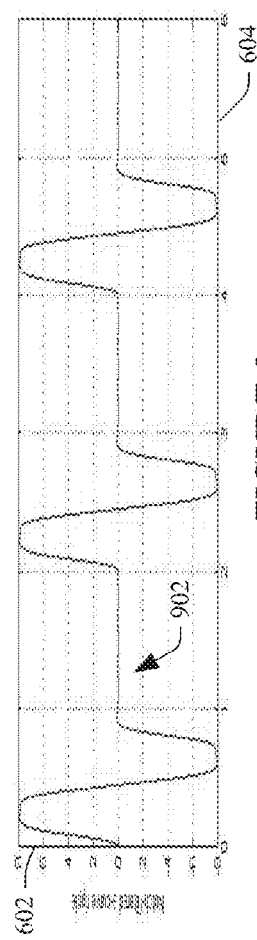
FIGURE 8
FIGURE 9

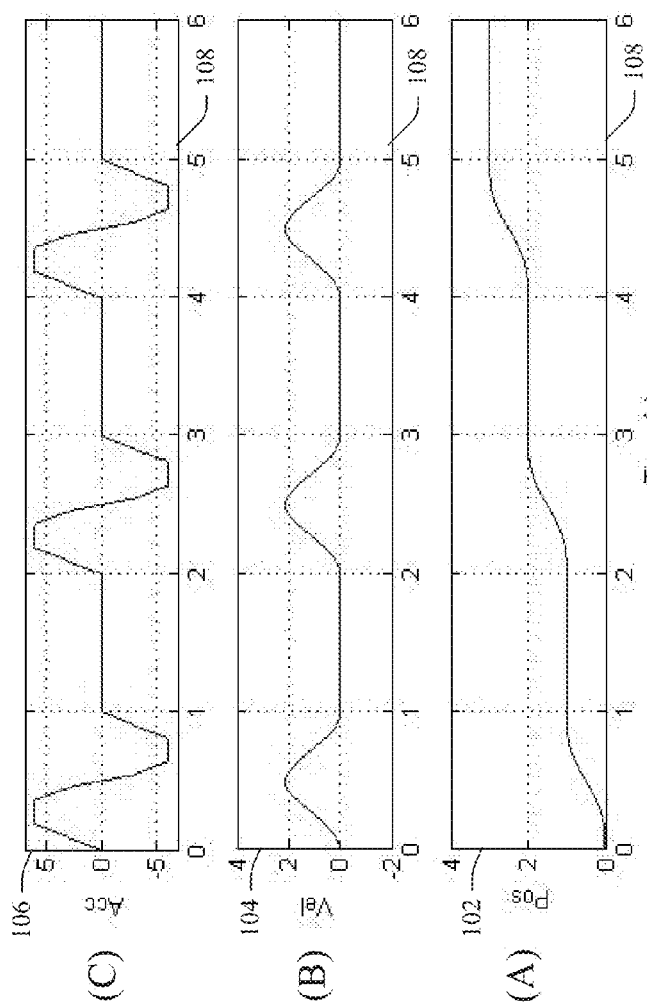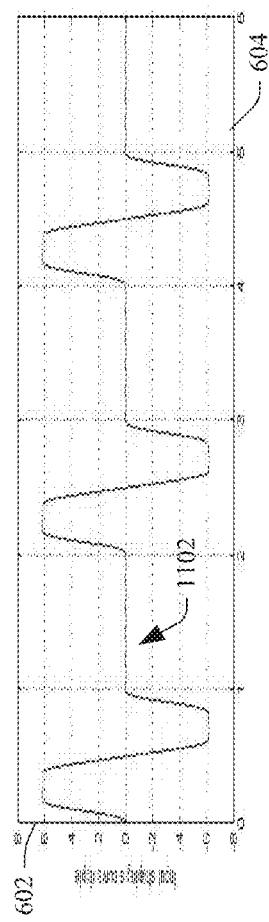
FIGURE 10
FIGURE 11

IMAGING SYSTEM SUBJECT SUPPORT MOTION ALGORITHM(S)

CROSS REFERENCE TO RELATED APPLICATIONS

This application is a national filing of PCT application Serial No. PCT/IB2012/050723, filed Feb. 16, 2012, published as WO 2012/110982 A1 on Aug. 23, 2012, which claims the benefit of U.S. provisional application Ser. No. 61/444,155 filed Feb. 18, 2011, which is incorporated herein by reference.

FIELD OF THE INVENTION

The following generally relates to translating a subject support of an imaging system in connection with axial and/or perfusion scans of a subject carried by the subject support, and is described with particular application to computed tomography (CT). However, the following is also amenable to subject supports for other imaging modalities such as positron emission tomography (PET), x-radiology, and/or other imaging modalities.

BACKGROUND OF THE INVENTION

A computed tomography (CT) scanner includes a rotating portion rotatably supported by a stationary portion. The rotating portion supports an x-ray tube, which emits radiation that traverses an examination region and an object or a subject therein, and a detector array that detects radiation traversing the examination region and generates projection data indicative of the detected radiation. A subject support supports the object or subject in the examination region. A reconstructor reconstructs the projection data and generates volumetric image data indicative of the portion of the object or subject in the examination region. One or more images can be generated based on the volumetric image data.

The subject support generally includes a base, which is affixed to the floor of the examination room and configured to move vertically with respect to the floor, and a tabletop, which is affixed to the base and is configured to translate horizontally, with respect to the base, in and out of the examination region. Both axial and perfusion scans require frequent tabletop translation; an axial scan is an imaging mode in which the tabletop moves the object or subject to each axial position for scanning, but does not move the object or subject during scanning, and a perfusion scan is an imaging mode in which the tabletop cycles the object or subject back and forth in the examination region during scanning.

Traditionally, tabletop translation for both axial and perfusion scans is accomplished using a trapezoidal or an s-curve motion algorithm. FIG. 1 illustrates an example s-curve motion algorithm for axial (step and shoot) scanning over three steps. In FIG. 1(A), a y-axis 102 represents tabletop position, in FIG. 1(B), a y-axis 104 represents tabletop velocity, and in FIG. 1(C), a y-axis 106 represents tabletop acceleration. In all three figures, an x-axis 108 represents time. As shown in FIG. 1(C), tabletop acceleration and deceleration for the s-curve motion algorithm includes abrupt variable ramp up and ramp down, for each step.

FIGS. 2 and 3 respectively illustrate example trapezoidal and s-curve motion algorithms for perfusion (cyclic) scanning In FIGS. 2(A) and 3(A), the y-axis 102 represents tabletop position, in FIGS. 2(B) and 3(B), the y-axis 104 represents tabletop velocity, and in FIGS. 2(C) and 3(C), the y-axis 106 represents tabletop acceleration, and the x-axis 108 in all six figures represents time. FIGS. 2(C) and 3(C) respectively show tabletop acceleration and deceleration with constant ramp up and ramp down and abrupt variable ramp up and ramp down, during each cycle.

The acceleration and deceleration profiles of the trapezoidal and s-curve motion algorithms of FIGS. 1-3 generally will result in tabletop vibration and motion of internal organs and tissue of the patient being scanned. More particularly, the tabletop is a lightly damped steel and composite structure with one or multiple resonant frequencies. Upon the moment of trapezoidal or s-curve point to point motion in the horizontal direction, the tabletop resonance can be aroused by the resonant component of the primary motion, resulting in undesired secondary motion or diving board vibration in the vertical direction. High acceleration and jerk due to the primary motion, when used cyclically in perfusion scans, may cause excessive human organ motion, resulting in an unpleasant patient experience.

Unfortunately, with axial scans, as the tabletop moving and settling time between scans becomes shorter and the intermitted travel becomes longer with wider coverage, motion acceleration and jerk will become greater, and, with perfusion scans, as the coverage becomes wider and the cycle time becomes shorter, perfusion scans can introduce greater secondary vibration. The secondary motion can be mitigated by use of a rigid based structure. However, with the conventional trapezoidal and s-curve algorithms, even with a stiff base structure, the amount of human organ motion and undesirable patient feeling generally cannot be mitigated.

SUMMARY OF THE INVENTION

Aspects of the present application address the above-referenced matters and others.

According to one aspect, an imaging system includes a subject support configured to carry a subject being imaged in an examination region of the imaging system and a subject support controller that positions the subject support and hence the subject in the examination region for scanning the subject based on a motion algorithm which reduces subject support vibration during scanning relative to a trapezoidal or s-curve motion algorithm, for a given translation duration and a given translation distance.

According to another aspect, a method includes determining a type of a scan for a subject based on a selected scan protocol of the scan. The type is one of an axial scan or a perfusion scan. The method further includes identifying a motion algorithm of interest, based on the type of scan, for a tabletop of a subject support of an imaging system used to perform the scan. The motion algorithm of interest is not a traditional trapezoidal and s-curve motion algorithm. The method further includes generating or retrieving a tabletop motion profile for the algorithm. The method further includes loading the tabletop motion profile into a subject support controller. The method further includes employing the subject support controller to control the tabletop during the scan of the subject based on the loaded tabletop motion profile.

According to another aspect, a method includes generating data indicative of a plurality of tabletop motion profiles. The motion profiles correspond to algorithms from a group consisting of: a sinusoidal harmonic axial algorithm; a profile shaped axial algorithm; a band pass filtered axial algorithm; a sinusoidal harmonic perfusion algorithm; and a filtered perfusion axial. The method further includes storing the plurality of tabletop motion profiles in storage accessible to a subject support controller configured to control a tabletop of a subject support during a scan. The method further includes selecting and employing one of the motion profiles based on a type of a scan for a scan protocol selected for scanning the subject.

According to another aspect, an imaging system includes a subject support configured to carry a subject being imaged in an examination region of the imaging system and a subject support controller that controls horizontal motion of the subject support based on a sinusoidal motion profile.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 8 illustrates sinusoidal position, velocity and acceleration motion profiles for a filtered time delay compensated axial motion algorithm for axial scanning.

FIG. 9 illustrates simulated vibration for the filtered compensation motion algorithm of FIG. 8 for axial scanning.

FIG. 10 illustrates sinusoidal position, velocity and acceleration motion profiles for a profile shaping motion algorithm for axial scanning.

FIG. 11 illustrates simulated vibration for the profile shaping motion algorithm of FIG. 10 for axial scanning.

DETAILED DESCRIPTION OF EMBODIMENTS

Figure 4:
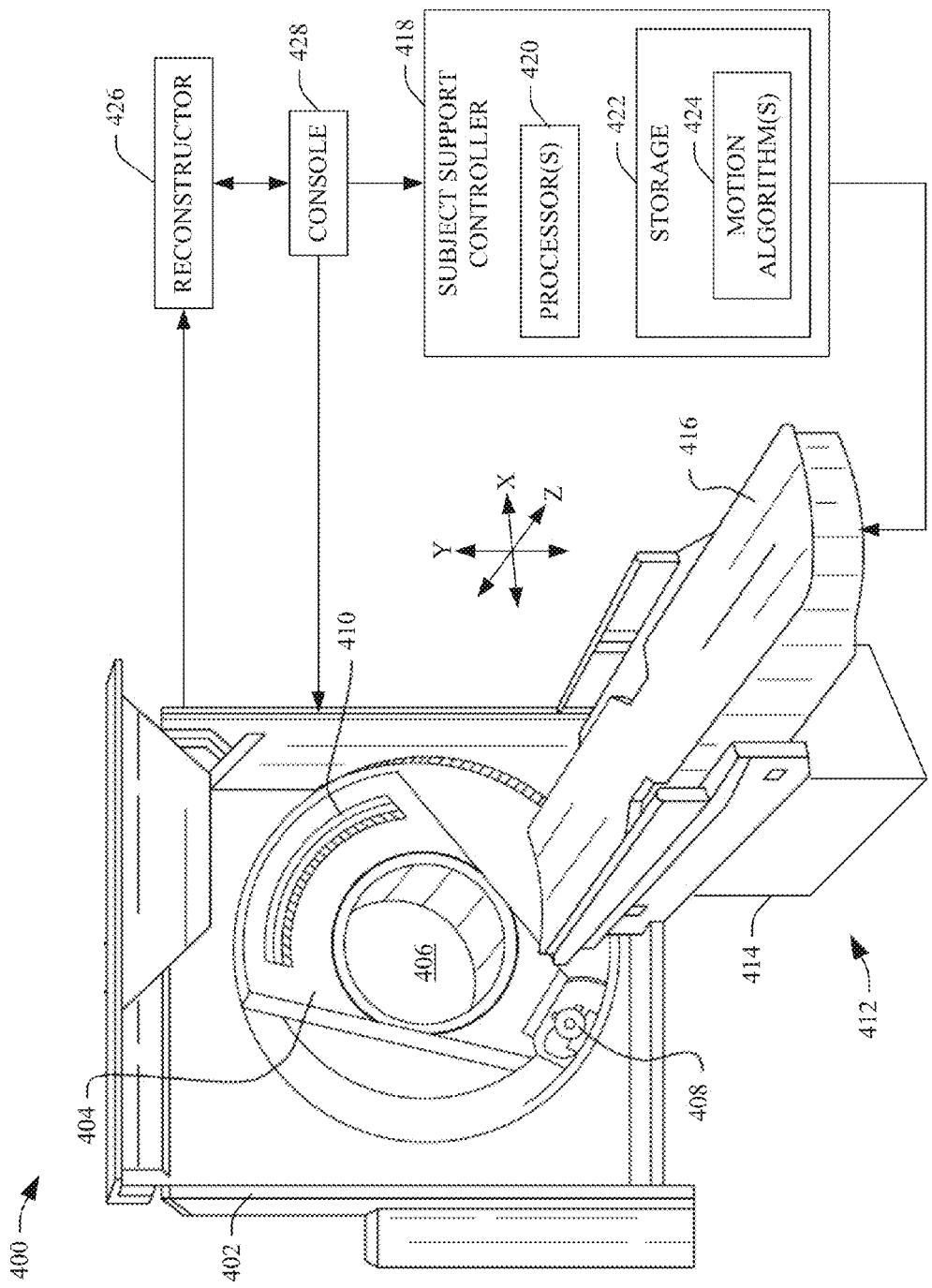
FIG. 4 schematically illustrates an example imaging system in connection with a subject support controller for controlling a subject support of the imaging system during scanning based on a subject support motion algorithm.

FIG. 4 schematically illustrates an imaging system 400 such as a computed tomography (CT) scanner. The imaging system 400 includes a stationary gantry 402 and a rotating gantry 404, which is rotatably supported by the stationary gantry 402. The rotating gantry 404 rotates around an examination region 406 about a longitudinal or z-axis. A radiation source 408, such as an x-ray tube, is supported by and rotates with the rotating gantry 404 around the examination region 406. The radiation source 408 emits radiation that is collimated by a source collimator to produce a generally fan, wedge, cone, or otherwise shaped radiation beam that traverses the examination region 406. A radiation sensitive detector array 410 includes a one or two dimensional array of detector pixels that respectively detect radiation that traverses the examination region 406 and generates an electrical signal indicative of the detected radiation.

A subject support 412, such as a couch, supports an object or subject in the examination region 406. The subject support 412 includes a base portion 414 and a tabletop 416, and is configured to position (vertically and/or horizontally) the object or subject, with respect to x, y, and/or z directions, in the examination region 406 for scanning For axial (step and shoot) scans, this includes moving the tabletop 416 and hence the object or subject to a predetermined position before an axial scan, maintaining a static position during the scan, and moving the tabletop 416 and hence the object or subject to next a position for a next axial when there is another axial scan to perform. This is repeated for each axial scan of the imaging procedure. For perfusion scans, this includes moving the tabletop 416 cyclically and hence the object or subject cyclically in coordination with scanning the object or subject.

A subject support controller 418 controls the movement of the subject support 412. The illustrated subject support controller 418 includes one or more processors 420 and computer readable storage medium 422 (e.g., physical memory), which stores computer readable instructions, which, when executed by the one or more processors 420 cause the controller 418 to transmit one or more control signals to control the subject support 412. The one or more processors 420 can additionally or alternative execute computer readable instructions carried in a signal, carrier wave or other transitory medium.

The illustrated storage medium 422 includes computer readable instructions such as one or more subject support motion algorithms 424. Examples of such algorithms include, but are not limited to, a sinusoidal harmonic axial motion algorithm, a feed-forward profile shaping axial motion algorithm, a feed-forward profile filtering with time delay compensation axial motion algorithm, a sinusoidal harmonic perfusion motion algorithm, a filtered perfusion motion algorithm, traditional axial and/or perfusion motion algorithms such as a trapezoidal or s-curve axial and perfusion motion algorithms, a combination of one or more of the above-noted motion algorithms, and/or one or more other motion algorithms.

As described in greater detail below, at least one of the non-traditional trapezoidal or s-curve axial and perfusion motion algorithms may mitigate at least one of tabletop vibration or internal subject motion, which, where the subject is a patient, may improve the experience of the patient and/or image quality. In one non-limiting instance, this is achieved while maintaining move duration, move distance, average speed, etc. relative to traditional trapezoidal or s-curve motion axial and perfusion motion algorithms, while providing jerk and acceleration motion profiles that minimize the undesired motion.

A reconstructor 426 reconstructs the signal generated by the detector array 408 and generates volumetric image data indicative of the examination region 406, including the portion of the object or subject therein. A general purpose computing system serves as an operator console 428, and includes an output device such as a display, an input device such as a keyboard, mouse, and/or the like, one or more processor and computer readable storage medium substantially similar to the storage medium 422. The console 428 allows the operator to control operation of the system 400, for example, allowing the operator to select a scan protocol (which may be associated with a default or user specified subject support motion algorithm), select or change the subject support motion algorithm, initiate scanning, etc.

Figure 5:
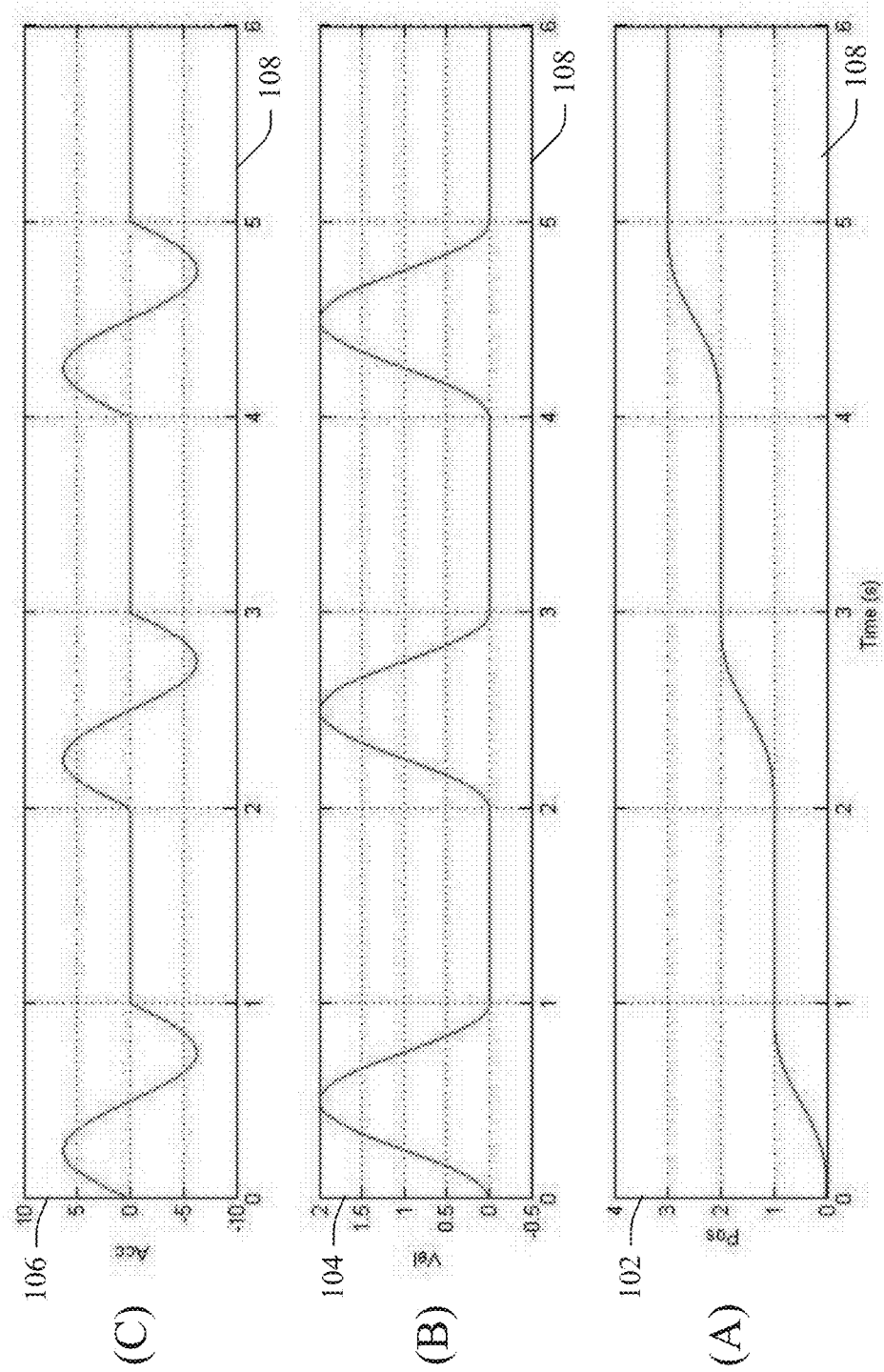
FIG. 5 illustrates sinusoidal position, velocity and acceleration motion profiles for a sinusoidal harmonic axial motion algorithm for axial scanning.
Figure 6:
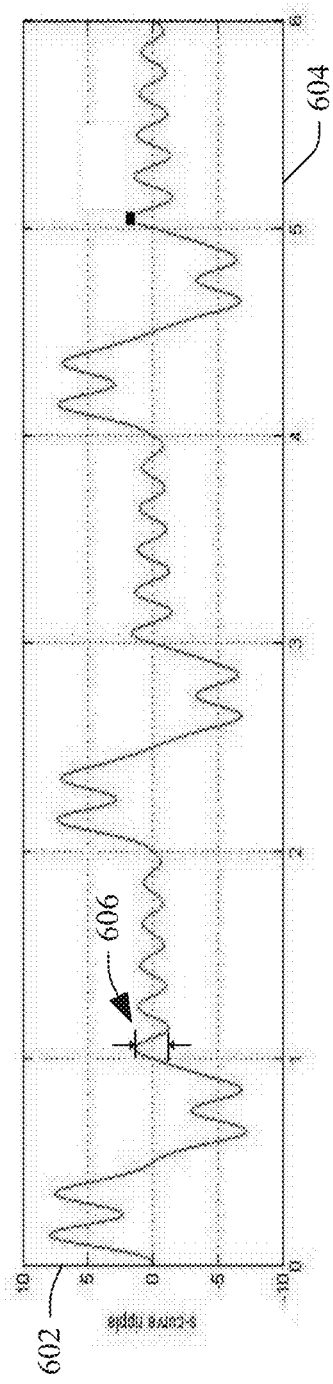
FIG. 6 illustrates simulated tabletop vibration for the sinusoidal harmonic axial motion algorithm of FIG. 5.
Figure 7:
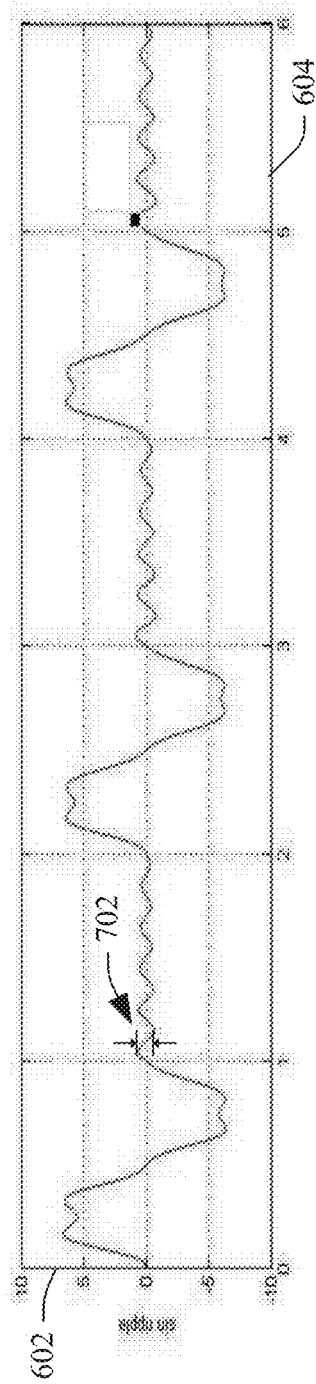
FIG. 7 illustrates simulated tabletop vibration for the s-curve axial motion algorithm of FIG. 1.

FIGS. 5, 8 and 10 illustrate a non-limiting set of subject support motion algorithms well-suited for axial scans, FIGS. 7, 9 and 11 illustrate simulated vibration for the set of algorithms, and FIG. 6 shows simulated vibration for a traditional s-curve axial motion algorithm.

Generally, a typical axial scan involves multiple steps of rest to rest motion. While the tabletop 416 comes to rest at a particular position, e.g., after each step move in the horizontal direction, inertia force of the step move excites the tabletop 416 and the base 414, causing a diving board like vibration of the tabletop 416, and the object or subject will vibrate in the vertical direction. The illustrated subject support 412 is a lightly damped metal and composite apparatus so resonance is inherent. The weight of the object or subject carried by the subject support 412, when coupled with acceleration, reduces the resonant frequency, and increase the inertia force required to complete the step motion, so the object or subject increases the amplitude of the diving board vibration. From the above, rest to rest moving is an external cause of the diving board vibration, and the low frequency resonance of the subject support 412 is an internal, or system, cause of the diving board vibration. With the illustrated subject support 412, the dominant frequency of the axial scan motion is smaller than the resonant frequency of the subject support even with the heaviest patient load.

Figure 1:
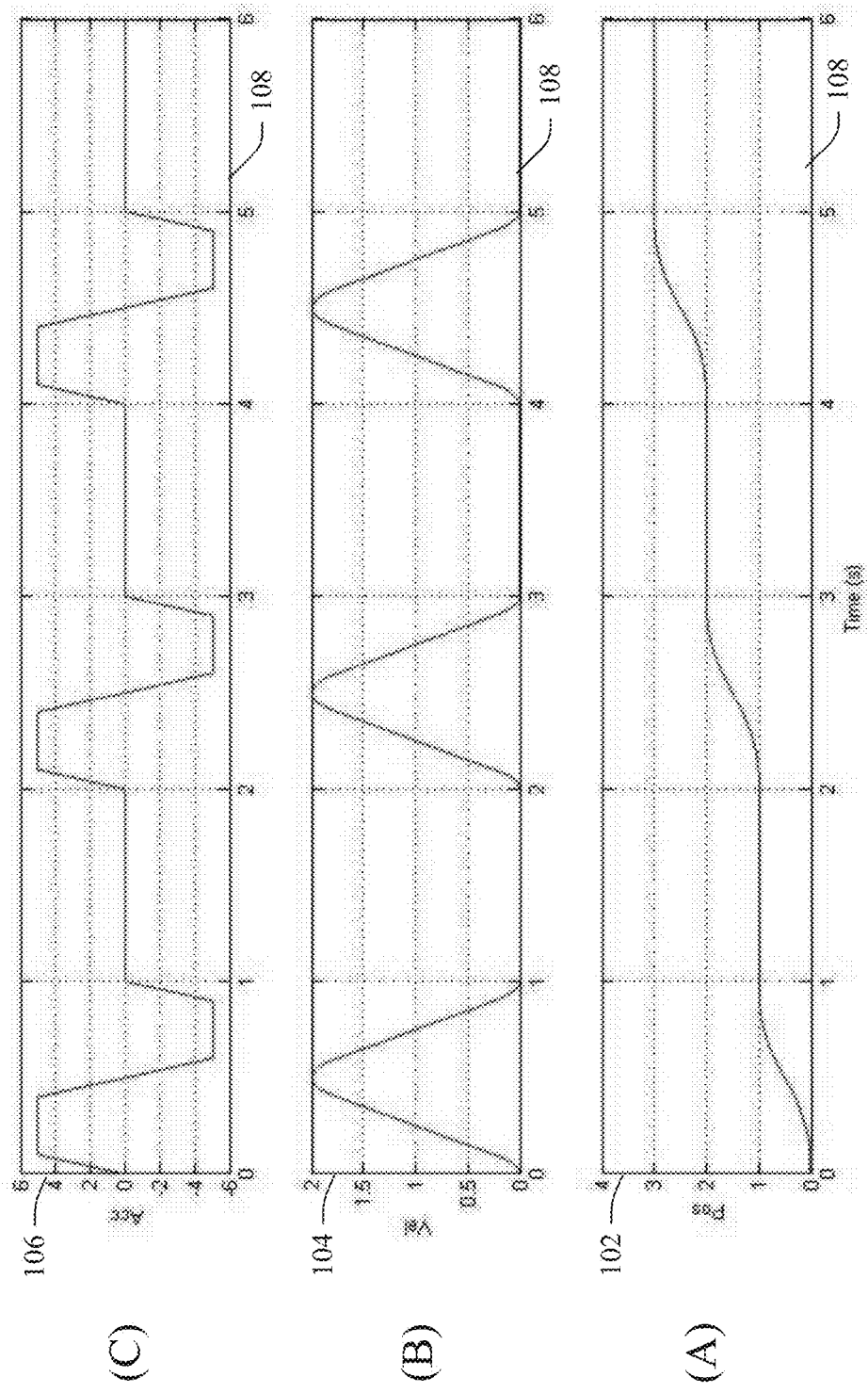
FIG. 1 illustrates a prior art s-curve motion algorithm for axial point to point scanning.

Initially referring to FIG. 5, an example sinusoidal motion algorithm with the identical time and distance as the s-curve motion algorithm of FIG. 1 is illustrated.

In FIG. 5(A), the y-axis 102 represents tabletop position, in FIG. 5(B), the y-axis 104 represents tabletop velocity and in FIG. 5(C), the y-axis 106 represents tabletop acceleration, and the x-axis 108 represents time in all three figures. Note that the tabletop velocity and position profiles in FIG. 5 are very similar to the tabletop velocity and position profiles of FIG. 1. However, the tabletop acceleration profiles of the sinusoidal harmonic algorithm of FIG. 5 is much smoother than the tabletop acceleration profile of FIG. 1, mitigating undesired motion.

FIGS. 6 and 7 respectively show simulated tabletop vibration for the s-curve axial motion algorithm of FIG. 1 and the sinusoidal axial motion algorithm of FIG. 5. In FIGS. 6 and 7, a y-axis 602 represents tabletop vibration and the x-axis 604 represents position. Note that the tabletop vibration for the sinusoidal harmonic axial motion algorithm of FIG. 7, during the time periods when the axial scans are acquired (i.e., between 1 and 2, 3 and 4, and 5 and 6), has a peak residue vibration 702 (e.g., 0.0846) that is about half (50%) of a peak residue vibration 606 (e.g., 1.664) for the s-curve axial motion algorithm of FIG. 1. In other embodiments, the peak 702 is about 25% to about 75% of the peak 606.

With both FIG. 6 and FIG. 7, the tabletop vibration dynamics are simulated based on the following transfer function $$SYS(s) = \frac{\omega_n^2}{s^2 + 2\gamma\omega_n + \omega_n^2} = \frac{986}{s^2 + 1.57\,s + 986}$$

which has a unit response for DC input, a resonant frequency $$\omega_n = 5\text{ Hz} = \frac{31.4\text{ rad}}{s},$$

and a damping ratio γ=0.025. Other transfer functions may also be used to characterize the tabletop.

Experimental results for motion distance of 33.6 mm, 39.2 mm, 50.5 mm, 60 mm, 68.6 mm, 76.4 mm with a load of 90 lb, 180 lb, 300 lb, and 450 lb for step and shoot scans are in agreement with the simulated data. By way of example, for a 300 lb load, the average vibration reduction of a sinusoidal move is about 47% compared with the s-curved move, and for a 450 lb load, average the vibration reduction of a sinusoidal move is about 46% compared with the s-curved move.

Turning to FIG. 8, an example filtered compensation motion algorithm for axial scanning is discussed.

In this example, a band-stop filter such as a notch filter or the like can be employed where the resonant frequency and damping factor of the subject support 412 are known or can be measured or estimated. Generally, a notch filter is a pole-zero cancelling technology that basically uses new zeros to cancel the resonant poles of the original system, and places new well damped poles to achieve a stable non-oscillatory response. Compared with a low pass filter, a notch filter generally introduces less delay at least in part due to phase lag concentricity to the resonant frequency and has much better vibration squeezing due to the stable poles and cancellation of resonant poles. The time delay to the original motion planning can be accounted for in order to scan a patient in the right rest intervals.

In FIG. 8(A), the y-axis 102 represents tabletop position after the time delay is factored in and the original s-curved position profile is filtered with the notch or other band pass filter, in FIG. 8(B), the y-axis 104 represents tabletop velocity and in FIG. 8(C), the y-axis 106 represents tabletop acceleration, and the x-axis 108 represents time in all three figures. In FIG. 9, the y-axis 602 represents tabletop vibration and the x-axis 604 represents position. Note that the simulated vibration has a peak residue vibration 902 of about or on the order of zero.

In the illustrated embodiment, the time delay compensation factor is expressed in terms of the resonant period $$T = \frac{2\pi}{\omega_n}$$

of the couch vertical dynamics. Using $$SYS(s) = \frac{\omega_n^2}{s^2 + 2\gamma\omega_n + \omega_n^2} = \frac{986}{s^2 + 1.57\,s + 986}$$

from above, an s-curved step motion of one second, one distance, and one move, and the following example notch filter $$\frac{s^2 + 1.57\,s + 986}{s^2 + 50\,s + 986}$$

to balance the resonance, the time delay introduced is T=0.2 second. This time delay is accounted for in the profiles of FIG. 8.

Turning to FIG. 10, an example profile shaping motion algorithm for axial scanning is discussed.

In this example, feed-forward input shaping is implemented by convolving a sequence of impulses, an input shaper, with a desired motion profile to produce a shaped motion profile input that produces self-cancelling command signal to limit the residue vibration of rest to rest move pattern. Similar to the filtered compensation motion algorithm discussed in FIG. 8, the input is the subject support resonant frequency and damping factor (which is used in this case to compute the gain and time location of the impulse functions), and time delay is accounted for in a digital implementation. However, compared with the filtered compensation motion algorithm, the input shaping filter introduces half of the notch-filter's delay, and has better residue vibration attenuation.

In FIG. 10(A), the y-axis 102 represents tabletop position, in FIG. 10(B), the y-axis 104 represents tabletop velocity and in FIG. 10(C), the y-axis 106 represents tabletop acceleration, and the x-axis 108 represents time in all three figures. In FIG. 11, the y-axis 602 represents tabletop vibration and the x-axis 604 represents position. Similar to the notch filtered axial motion algorithm, the simulated vibration for the input shaping axial motion algorithm has a peak residue vibration 1102 of about or on the order of zero.

For system with transfer function of $$SYS(s) = \frac{\omega_n^2}{s^2 + 2\gamma\omega_n + \omega_n^2} = \frac{986}{s^2 + 1.57\,s + 986},$$

the time domain expression of the input shaper can be expressed as $M(t)=C_1\delta(t)+C_1\delta(t-T_d)$, wherein $$C_1 = \frac{1}{1+K} \text{ and } C_2 = \frac{K}{1+K}$$

are coefficients of the input shaper, $$K = \exp\left(\frac{-\gamma\Pi}{\sqrt{1-\gamma^2}}\right), \quad Td = \frac{T}{2} = \frac{\Pi}{\omega_n}$$

is the time delay factor, and $\delta(t)$ is the unit impulse function. For a given input motion profile $x(t)$, the input shaped motion profile is $x_m(t)=x(t)*M(t)$, where "*" denotes mathematical convolution operation. In one instance, the above time domain convolution can be converted to continuous time transfer function, which is commonly used in simulation, and then the continuous time delay transfer function can be approximated with a continuous rational function. In another instance, the continuous time domain input shaper can be directly converted to discrete the time domain transfer function $x_m(z)=x(z)(C_1+C_2z^{-n})$ where n is the integer part of the value $$\frac{T_d}{\Delta t}$$

with sampling period $\Delta t$ and $C_1+C_2z^{-n}$ is the feed-forward digital input shaping filter. Due to the time delay of the input shaping, the original move time has to be shortened $T_d$ time and the acceleration is increased.

Figure 12:
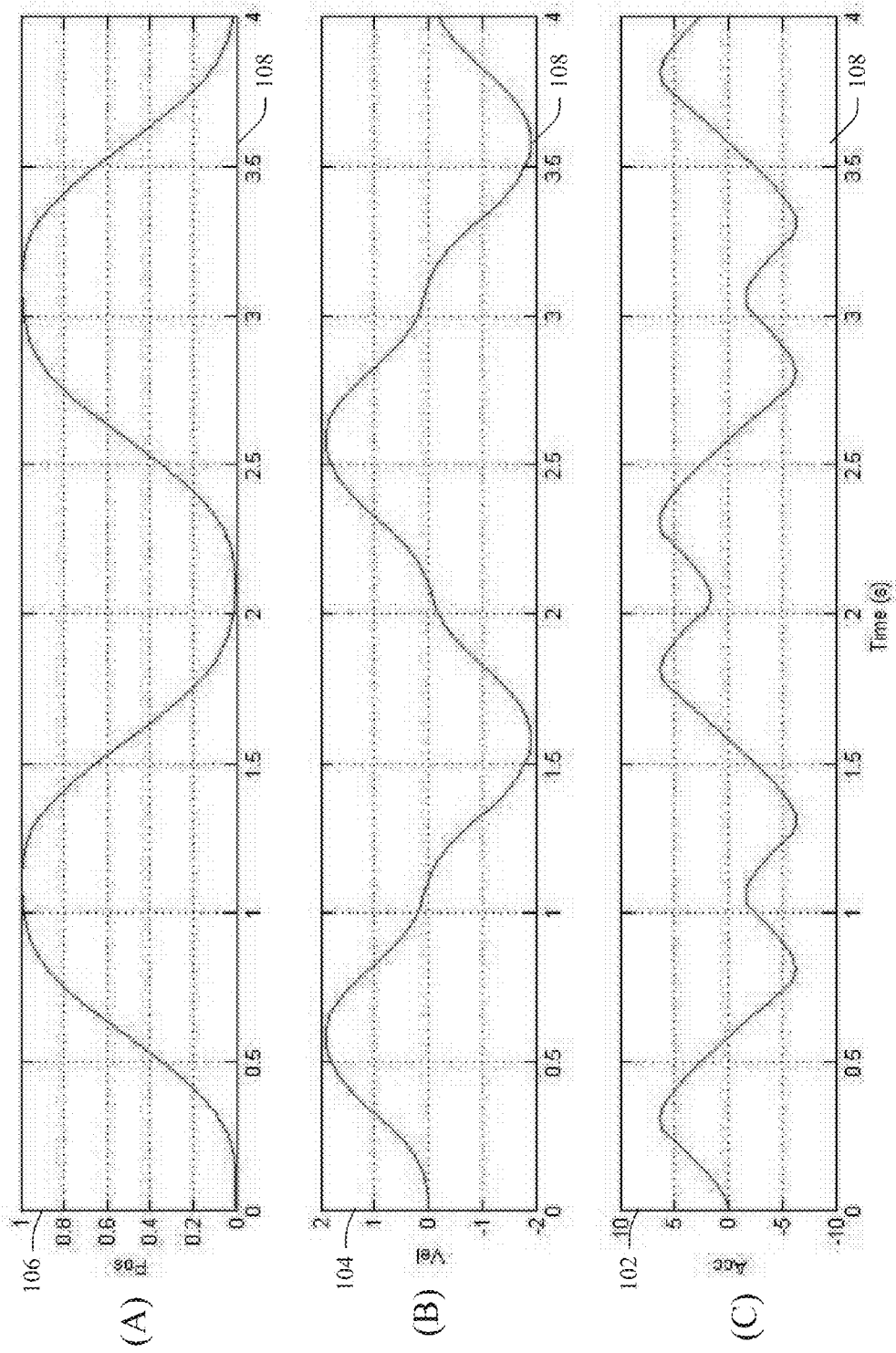
FIG. 12 illustrates sinusoidal position, velocity and acceleration motion profiles for a filtered s-curve motion algorithm for perfusion scanning.
Figure 13:
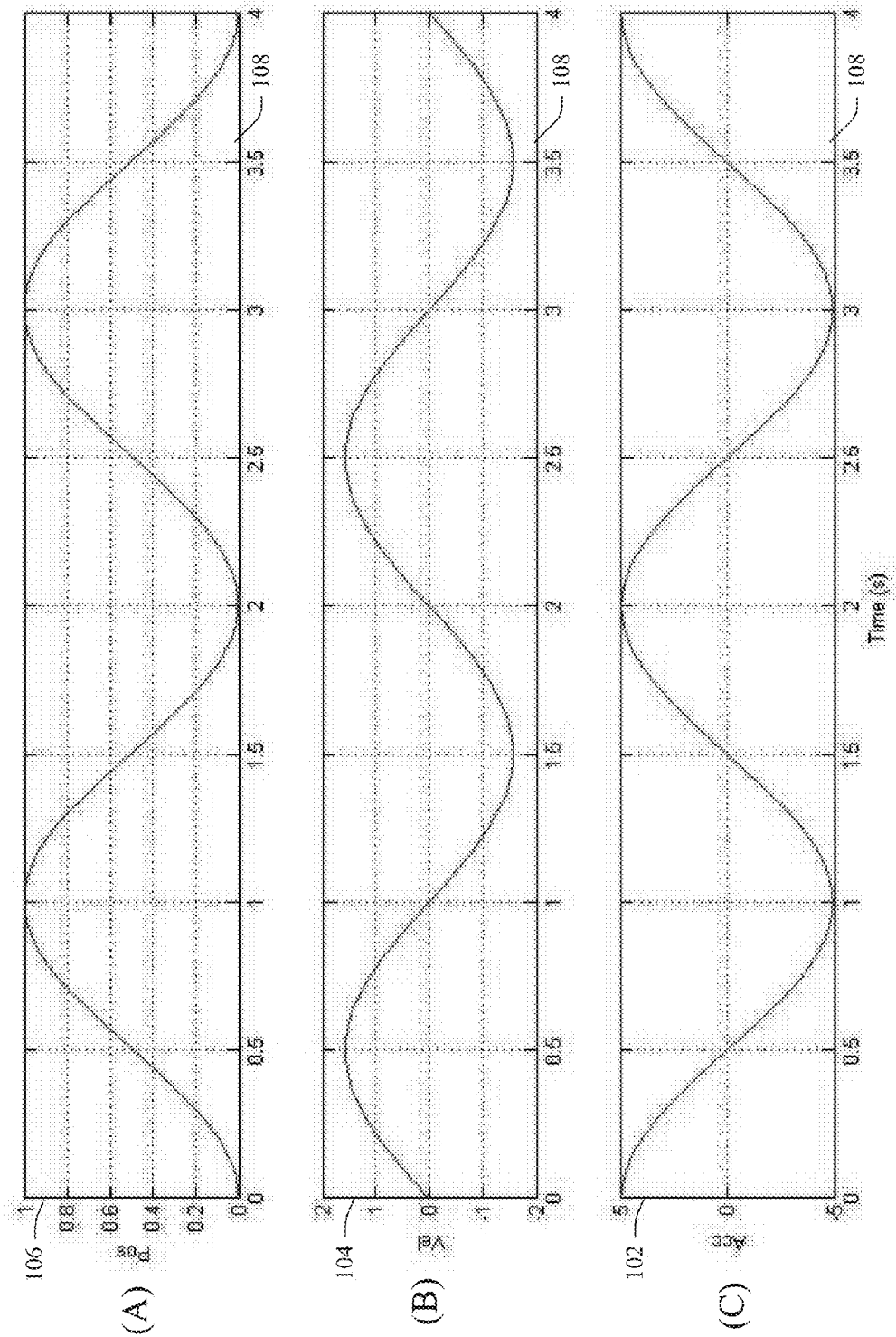
FIG. 13 illustrates sinusoidal position, velocity and acceleration motion profiles for a sinusoidal harmonic algorithm for perfusion scanning.

FIGS. 12 and 13 illustrate a non-limiting set of subject support motion algorithms well-suited for at least perfusion scans.

For a perfusion scan, a general concern is patient comfort and the impact of organ motion in horizontal direction on image quality, and since the patient lies on the tabletop 416, patient comfort is affected by the force pattern introduced by the tabletop friction, i.e., the tabletop's acceleration and jerk and its frequency pattern of the primary motion. Generally low frequency and low acceleration will result in lower jerk and better patient feeling.

Figure 2:
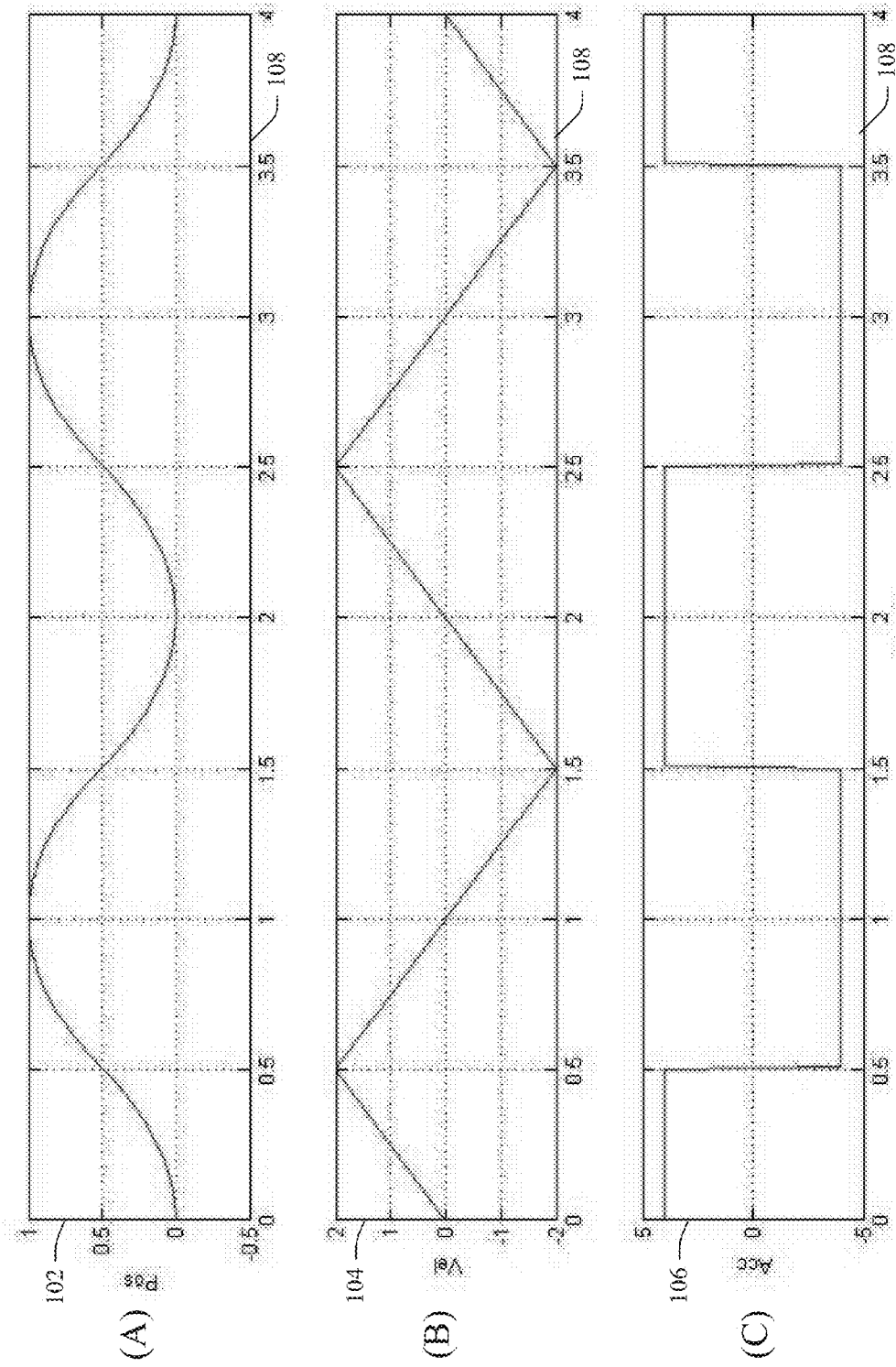
FIG. 2 illustrates a prior art trapezoidal motion algorithm for perfusion cyclic scanning.
Figure 3:
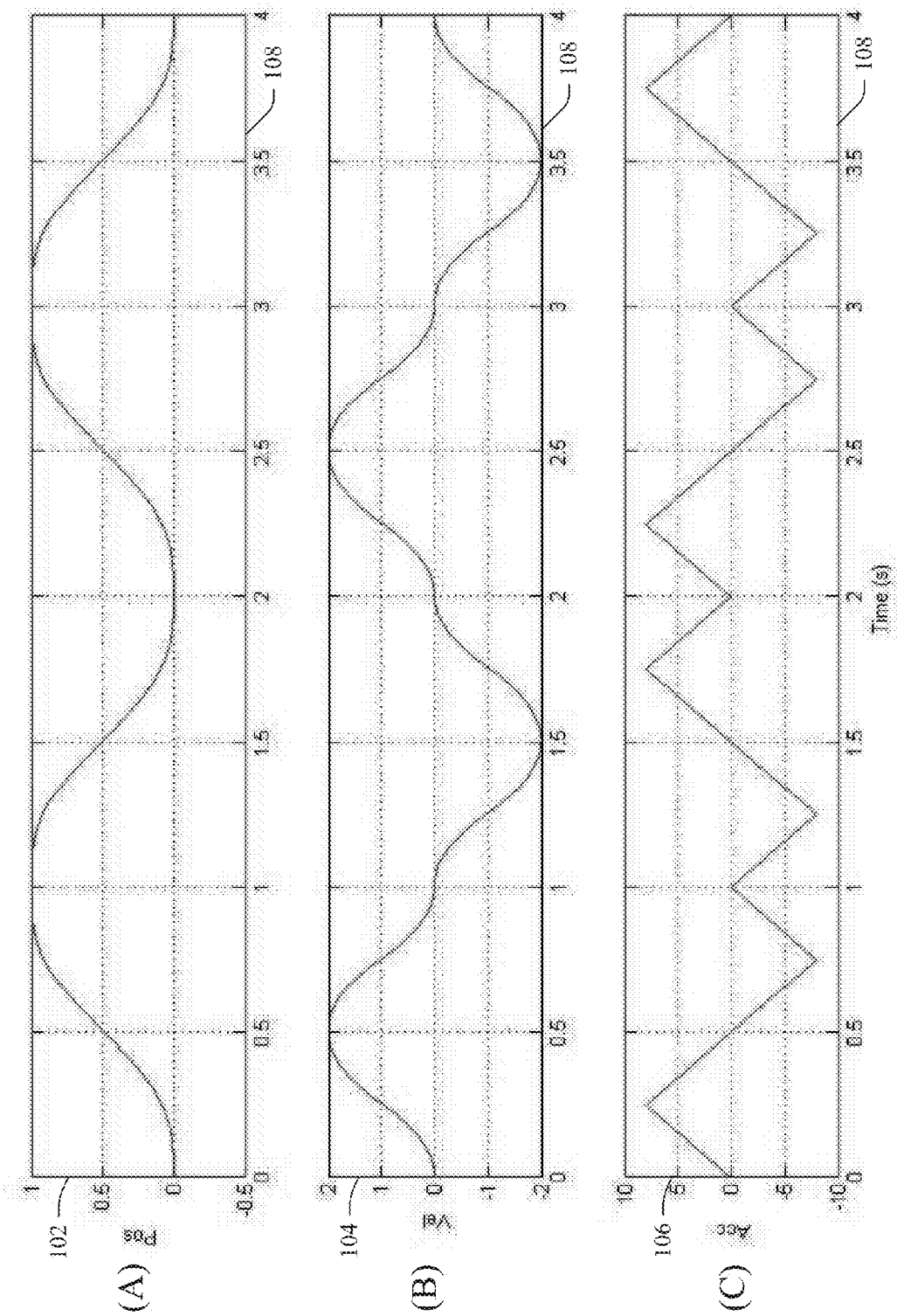
FIG. 3 illustrates a prior art s-curve motion algorithm for perfusion cyclic scanning.

FIG. 12 shows a filtered point-to-point s-curve perfusion motion algorithm. In FIG. 12(A), the y-axis 102 represents tabletop position, in FIG. 12(B), the y-axis 104 represents tabletop velocity and in FIG. 12(C), the y-axis 106 represents tabletop acceleration, and the x-axis 108 represents time in all three figures. FIG. 13 shows a sinusoidal harmonic perfusion motion algorithm. In FIG. 13(A), the y-axis 102 represents tabletop position, in FIG. 13(B), the y-axis 104 represents tabletop velocity and in FIG. 13(C), the y-axis 106 represents tabletop acceleration, and the x-axis 108 represents time in all three figures. As can seen from FIGS. 12, 13, 2 and 3, the tabletop acceleration of both the filtered point-to-point s-curve perfusion motion algorithm (FIG. 12) and the sinusoidal harmonic perfusion motion algorithm (FIG. 13) are smoother and thus result in less jerk and patient discomfort relative to the tabletop acceleration of the trapezoidal perfusion motion algorithm (FIG. 2) and the point-to-point s-curve perfusion motion algorithm (FIG. 3).

For the filtered point-to-point s-curve perfusion motion algorithm (FIG. 12), a first order low pass filter $$\left(\text{e.g., } \frac{\omega_c}{s+\omega_c}\right)$$

or higher order filter can be applied to the non-harmonic motion to alleviate the acceleration and jerk level of the non-harmonic motion to obtain better patient feeling. Note that the cut-off frequency $\omega_c$ of the low pass filter has to be carefully chosen. Too high cut-off frequency, the low pass filter has no motion smoothing effect, while too low cut-off frequency will produce too much motion coverage reduction and phase lag. For perfusion scanning, the phase lag is not an issue (like it is in axial scanning, as described above) as long as it is repetitive and constant, but the excessive coverage reduction has to be compensated. Around four (4) times cut-off frequency of the perfusion cycle frequency can be used to the low pass filter to balance the coverage cutting and motion smoothing effect. The effect of the low pass filter on the point to point s-curve perfusion motion phase lag and amplitude cutting can be seen in FIG. 12 where the cut-off frequency is 2 Hz for a 0.5 Hz perfusion cycle (i.e., a one (1) second end-to-end move, or a period of two (2) seconds).

Figure 14:
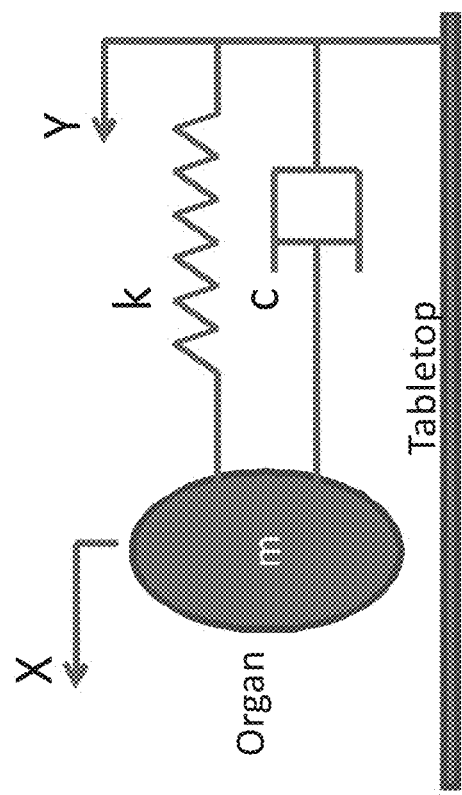
FIG. 14 illustrates an example model for modeling the elastic and viscous nature of soft tissue for the perfusion motion algorithms.

FIG. 14 shows an example model that can be used to model the elastic and viscous nature of soft tissue for the perfusion motion algorithms.

The model assumes human organ as a passive, stable, and low pass systems, which may or may not have resonance, and is not sensitive to high frequency excitation. In this model, the relative human organ motion "X-Y" will be small if the organ position X can follow the tabletop position Y closely, where 'm' is the mass of the organ, 'k' is the stiffness of the tissue, and 'c' is the damping coefficient of the organ to external perturbation. Based on this model, for a harmonic perfusion motion profile, which only has one very low frequency component, the motion of the organ will follow the tabletop motion closely without extra motion mismatch or lag, while the motion mismatch will be much larger for the same amplitude and frequency non-harmonic motion profile because of its inherent high-frequency harmonic component of the non-sinusoidal motion profile according to the Fourier transformation theory, and human organ dynamics will filter the high frequency out. Of course, other models can additionally and/ or alternatively be used.

Experiments verified the impact of the different perfusion motion profiles in terms of water ripple in the half-filled fish tank that is placed on the couch tabletop. Four kinds of motion profile: back and forth trapezoidal motion so triangle speed, point to point trapezoidal motion with 50 ms delay, point to point trapezoidal motion with 255 ms smoothing factor and 50 ms delay so basically a s-curve motion, and back and forth sinusoidal motion were tested with cycle time around 1 second and cycle distance around 160 mm. The results show all other motion profiles except sinusoidal motion cause very dramatic water ripple. Other experiments showed the impact of the smaller acceleration level with 1.5 seconds and 2 seconds cycle time sinusoidal motion. With these experiments, barely any water ripple could be seen in case of 160 mm travel and 1.5 seconds cycle time sinusoidal motion. The experiments further showed that sinusoidal motion with even longer coverage (higher average speed and acceleration) still achieves much smaller water ripple. Further experiments included human subjects for determining true human feeling for the sinusoidal perfusion motion algorithm profile with 180 mm coverage of 1 second cycle time that lasts 1 minute, ends up 886 mm/s² peak acceleration and 282 mm/s peak speed. The results showed no dizziness or unpleasant feeling for the subjects. The long coverage and short cycle time combination with other perfusion motion algorithms is a concern for point to point back and forth perfusion scan.

With respect to the example motion algorithms discussed herein, the sinusoidal motion algorithms have a 90 degree phase shift between the velocity and acceleration curves, which may result in relatively smaller drive power capacity compared with the other simultaneous peak speed and peak acceleration motion profile, because speed corresponds to voltage for motor drive, acceleration means torque so drive current, and power is derived by speed times force or by voltage times current. Smaller power drive means cost saving opportunity. Furthermore, different from the zero speed, zero acceleration at beginning and end of point to point s-curve back and forth perfusion, the initial and end speed of the sinusoidal motion at the beginning and end is zero, but the sinusoidal acceleration is peak at both ends. This is a unique feature of the sinusoidal perfusion motion profile. If optimal or desired sinusoidal perfusion motion cannot be implemented with a particular subject support and/or motion controller, the sub-optimal motion profile still satisfies a 90 degree phase shift of speed and acceleration curve to get the smallest acceleration level and smoothest acceleration change to shore up patient feeling.

The following provides a general summary of various non-limiting motion algorithms discussed herein.

For feed-forward input shaping (FIG. 8) and band pass filtering (FIG. 10) axial motion algorithms, the time delay is factored in first to calculate the acceleration profile, then the acceleration is integrated to get speed, which is integrated to get position, and then the profile is sampled and digitally shaped or filtered to generate the modified motion profile for couch primary motion input. For feed-forward low pass filtering of the perfusion motion profile (FIG. 12), the low pass filter cut-off frequency is calculated first, and then the original profile is digitally sampled and low pass filtered to generate the filtered motion profile.

The harmonic motion algorithms for the axial scan (FIG. 5) and perfusion scan (FIG. 13) are similar in theory but different in implementation. The pattern of axial scan move includes move duration, stop duration for scan, then next move duration, and stop duration, and more dependent on the move steps. The pattern of perfusion scan includes move, then back move, then move, and more dependent on the perfusion cycles, and no intermittent stop duration. The harmonic single step point to point move of axial scan includes a full wave of acceleration cycle to begin and end the move with initial zero jerk, acceleration and speed, which is essential to minimize the secondary motion. The harmonic cyclic move of perfusion scan includes a half wave of acceleration and speed cycle due to the repetitive feature of the motion.

Figure 15:
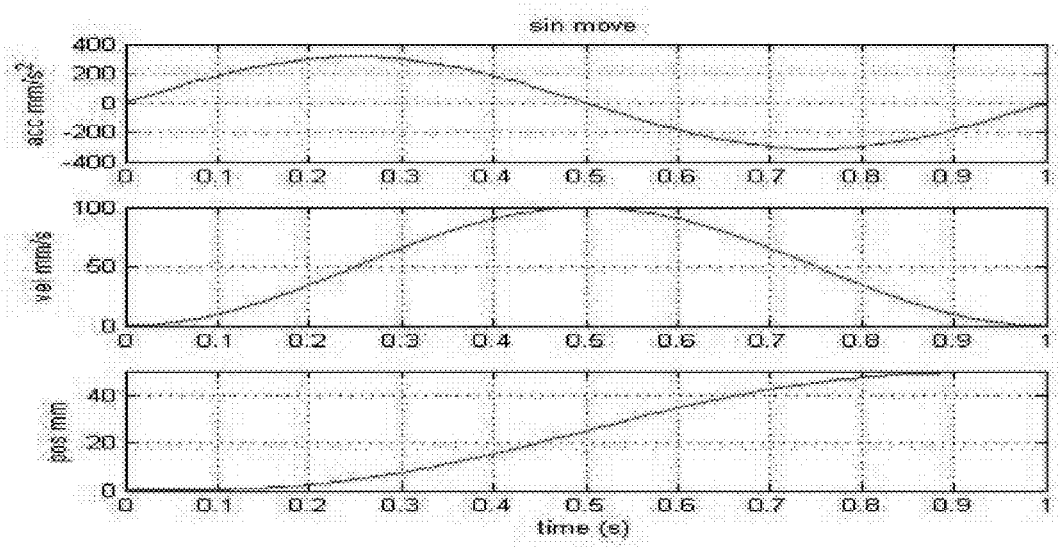
FIG. 15 shows an example motion profile of a harmonic single step axial scan.

A non-limiting harmonic motion profile for an axial scan can be based on, $$s(t) = A\left\{\frac{t}{T} - \frac{1}{2\pi}\sin\left(2\pi\frac{t}{T}\right)\right\};$$

$$v(t) = \frac{A}{T}\left\{1 - \cos\left(2\pi\frac{t}{T}\right)\right\};$$

$$a(t) = \frac{2\pi A}{T^2}\sin\left(2\pi\frac{t}{T}\right)$$

and, wherein A represents a single step move distance, T represents the move period, s represents the real time position, υ represents the real time speed, α represents s the real time acceleration, and t represents the time index. FIG. 15 shows an example motion profile (acceleration, velocity and position) for a single step harmonic point to point motion algorithm for an axial scan with A=50 mm and T=1 s.

Figure 16:
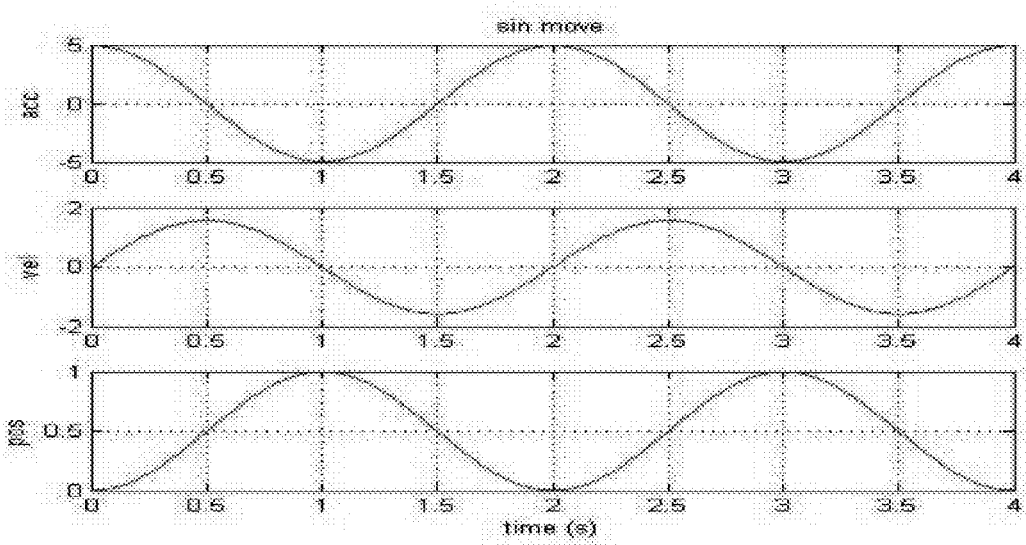
FIG. 16 shows an example motion profile of a harmonic perfusion scan.

A non-limiting harmonic motion profile for a perfusion scan can be based On $$s(t) = \frac{A}{2}\left(1 - \cos\left(\pi\frac{t}{T}\right)\right);$$

$$v(t) = \frac{A}{2} \cdot \frac{\pi}{T}\sin\left(\pi\frac{t}{T}\right)$$

and $$a(t) = \frac{A}{2} \cdot \left(\frac{\pi}{T}\right)^2 \cos\left(\pi\frac{t}{T}\right),$$

wherein A represents cyclic move (end to end distance) distance, T represents the (end to end time) move period, s represents the real time position, υ represents the real time speed, α represents s the real time acceleration, and t represents the time index. FIG. 16 shows an example motion profile (acceleration, velocity and position) for a harmonic perfusion scan with A=1 mm and T=1 s.

To command a harmonic motion, the subject support controller 418 can generate a motion reference profile in advance, which is an array of position and time pairs. Where the controllers 418 is not capable of the computing a sinusoidal function online, a look up table and be generated and stored for the controller 418. By way of example, the point to point harmonic move trajectory of unit distance and unit period with 100 (or some other number) samples can be determined offline dependent on the controller's memory size. In one instance, the trajectory is an array of 100 components. In this instance, each component can be represented as two parameters, a position count parameter and a time index parameter. Such trajectory data can be saved into the storage 422 of the controller 418 as a lookup table. If the desired move period is X rather than unit second, then the time index is multiplied by X. If the desired move distance is Y rather than unit length, then the position count is multiplied by Y. Two harmonic motion modes can be created, one for single step move, and the other for the cyclic move. Each harmonic motion function will have a set of functional variables of move distance and move time.

Although the motion algorithms are primarily discussed in connection with CT, it is to be understood that one or more of them can be employed in connection with one or more other imaging modalities such as PET, X-ray, etc. In one instance, the one or more algorithms can be used to mitigate and/or minimize the induced secondary vibration and/or human organ motion and to improve patient feeling. The one or more algorithms can also be used with other single step or multiple steps or back and forth point to point positioning scenarios with or without rest time in between which concern the unnecessary residue motion.

Figure 17:
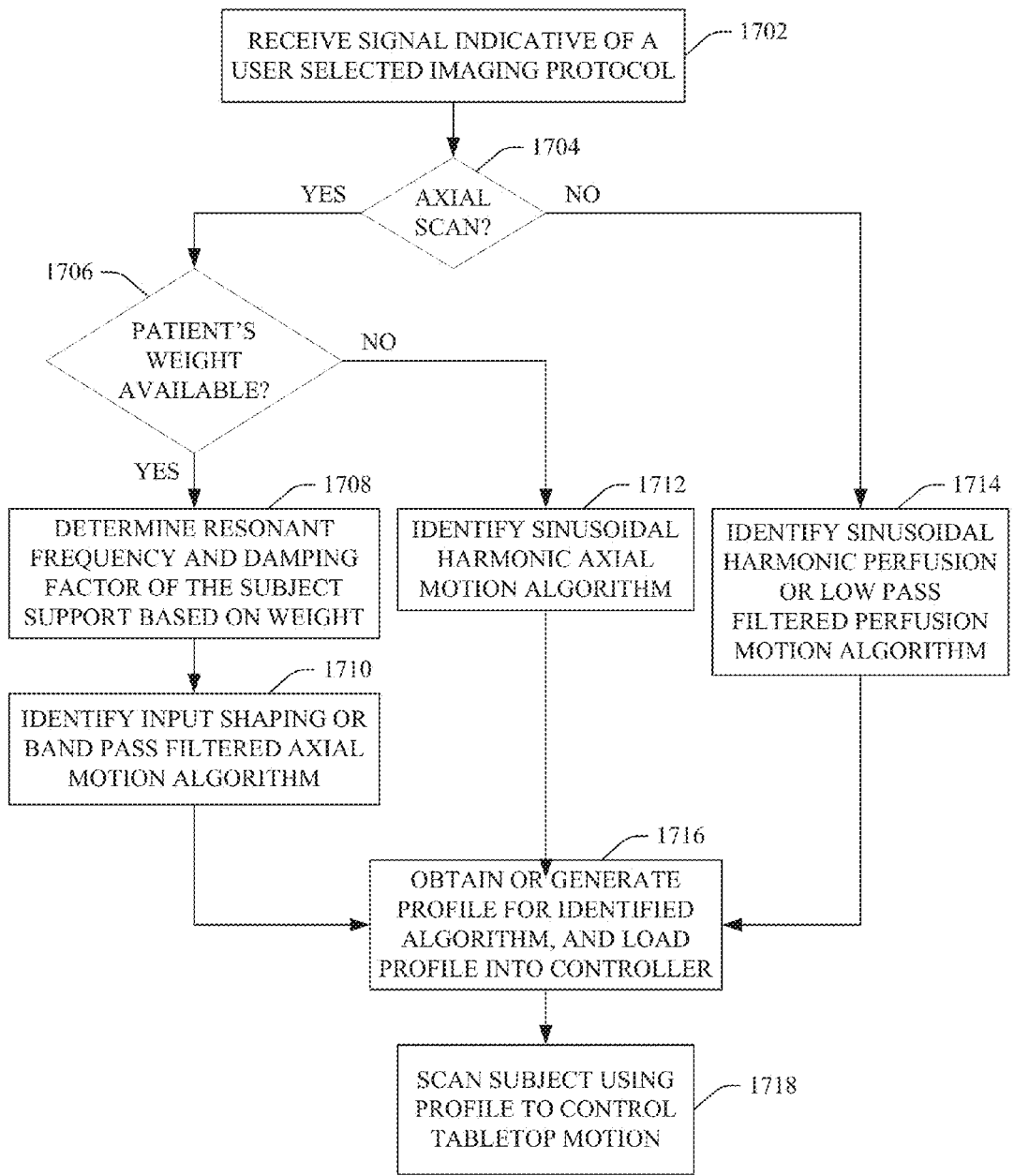
FIG. 17 illustrates an example method for determining a tabletop motion algorithm for a selected imaging protocol.

FIG. 17 illustrates an example method for determining a tabletop motion algorithm for a selected imaging protocol.

It is to be appreciated that the ordering of the acts in the methods described herein is not limiting. As such, other orderings are contemplated herein. In addition, one or more acts may be omitted and/or one or more additional acts may be included.

At 1702, a signal indicative of a user selected imaging protocol is received. The selected imaging protocol may be an axial or a perfusion scan.

At 1704, it is determined whether the selected protocol is an axial or perfusion scan protocol.

At 1706, where the selected protocol is for an axial scan, it is determined whether the patient's weight is known and available. Such information may be part of the electronic patient information, entered by a clinician, and/or dynamically measured, for example, via a scale or the like incorporated into the subject support 412 or otherwise.

At 1708, where the selected protocol is for an axial scan and the patient's weight is known, a resonant frequency and damping factor of the subject support 412 are determined based at least on the patient's weight. This may include mapping the patient's weight to a look up table (LUT) that cross references patient weight with subject support resonant frequency and damping factor. The LUT can be stored in the storage 422 or other storage.

At 1710, where the resonant frequency and damping factor are determined, the processor 420 identifies one of the feed-forward input shaping (FIG. 8) or the band pass filtered (FIG. 10) axial motion algorithms.

At 1712, where the selected protocol is for an axial scan and the patient's weight is not known, the processor 420 identifies the sinusoidal harmonic axial scan motion algorithm (FIG. 5).

At 1714, where the selected protocol is for a perfusion scan, the processor 420 identifies one of the feed-forward low pass filtered perfusion motion algorithm (FIG. 12) or the perfusion harmonic motion algorithm (FIG. 13).

At 1716, a profile for the identified tabletop motion algorithm is obtained or generated, and loaded by the subject support controller 418. The identified motion profile can dynamically generated, retrieved from storage 422 or other storage, derive, or otherwise obtained.

At 1718, the scan is performed using the profile to control the motion of the tabletop 416.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
    a subject support configured to carry a subject being imaged in an examination region of the imaging system; and
    a subject support controller that positions the subject support and hence subject in the examination region for scanning the subject based on a motion algorithm which reduces subject support vibration during scanning relative to a trapezoidal and s-curve motion algorithm, for a given translation duration and a given translation distance wherein the motion algorithm includes a time compensated band pass filtered s-curve axial motion algorithm.

2. The imaging system of claim 1, wherein the motion algorithm reduces motion of internal anatomical structure of the subject during scanning relative to the trapezoidal and s-curve motion algorithms, for the given translation duration and the given translation distance.

3. The imaging system of claim 1, wherein the motion algorithm reduces subject support jerk relative to the trapezoidal and s-curve motion algorithm, for the given translation duration and the given translation distance.

4. The imaging system of claim 1, wherein the motion algorithm is a sinusoidal harmonic axial or perfusion motion algorithm, having a sinusoidal shaped subject support acceleration profile.

5. The imaging system of claim 4, wherein the sinusoidal harmonic axial motion algorithm induces about half as much vibration in the subject support relative to the s-curve motion algorithm.

6. The imaging system of claim 1, wherein the motion algorithm is a low pass filtered s-curve perfusion motion algorithm.

7. The imaging system of claim 6, wherein the subject support controller generates a motion profile of the motion algorithm by sampling and low pass filtering a predetermined profusion motion profile based on a predetermined cut-off frequency.

8. The imaging system of claim 1, wherein the motion algorithm is a feed-forward input shaping axial motion algorithm.

9. The imaging system of claim 8, wherein the motion algorithm is based on a resonant frequency and damping factor of the subject support, which are determined based on a weight of the subject.

10. The imaging system of claim 9, wherein the subject support includes a scale for determining the weight of the subject when the subject is on the subject support.

11. The imaging system of claim 8, wherein the subject support controller dynamically generates a motion profile of the motion algorithm by adding a time delay into a position profile and input shaping or band pass filtering the time-delayed position profile.

12. The imaging system of claim 1, wherein the motion algorithm is a sinusoidal harmonic axial algorithm with the following position, velocity and acceleration profiles:

$$s(t) = A\left\{\frac{t}{T} - \frac{1}{2\pi}\sin\left(2\pi\frac{t}{T}\right)\right\};$$

$$v(t) = \frac{A}{T}\left\{1 - \cos\left(2\pi\frac{t}{T}\right)\right\}; \text{ and}$$

$$a(t) = \frac{2\pi A}{T^2}\sin\left(2\pi\frac{t}{T}\right),$$

wherein s represents a real-time subject support position, v represents a real-time subject support velocity, α represents a real-time subject support acceleration, A represents a single step subject support move distance, T represents a subject support move period, and t represents a time index.

13. The imaging system of claim 1, wherein the motion algorithm is a sinusoidal harmonic perfusion algorithm with the following subject support position, velocity and acceleration profiles:

$$s(t) = \frac{A}{2}\left(1 - \cos\left(\pi\frac{t}{T}\right)\right);$$

$$v(t) = \frac{A}{2} \cdot \frac{\pi}{T}\sin\left(\pi\frac{t}{T}\right)$$

and $$a(t) = \frac{A}{2} \cdot \left(\frac{\pi}{T}\right)^2 \cos\left(\pi\frac{t}{T}\right),$$

wherein s represents a real-time subject support position, v represents a real-time subject support velocity, α represents a real-time subject support acceleration, A represents cyclic end-to-end subject support move distance, T represents end-to-end subject support move time, and t represents a time index.

14. A method, comprising:
  determining a type of a scan for a subject based on a selected scan protocol of the scan, wherein the type is one of an axial scan or a perfusion scan;
  identifying a motion algorithm of interest, based on the type of scan, for a tabletop of a subject support of an imaging system used to perform the scan, wherein the motion algorithm of interest is not a traditional trapezoidal and s-curve motion algorithm;
  generating or retrieving a tabletop motion profile for the algorithm from a plurality of algorithms including at least a time compensated axial algorithm;
  loading the tabletop motion profile into a subject support controller; and
  employing the subject support controller to control the tabletop during the scan of the subject based on the loaded tabletop motion profile.

15. The method of claim 14, wherein the identified motion algorithm is a sinusoidal harmonic axial or perfusion algorithm.

16. The method of claim 14, further comprising:
  receiving a signal indicative of a weight of the subject;
  determining a resonant frequent and a damping ratio of the subject support based on the received weight; and
  generating the motion algorithm based on the resonant frequent and the damping, wherein the scan is an axial scan and the motion algorithm is one of a profile shaping motion algorithm or a profile filtered motion algorithm.

17. The method of claim 16, wherein the motion algorithm includes a time delay that compensates for a time delay introduced by the shaping.

18. The method of claim 16, wherein the motion algorithm reduces at least one of subject support vibration, subject support jerk, or subject internal motion, during scanning, relative to a trapezoidal or s-curve motion algorithm, for a given translation duration and a given translation distance.

19. A method, comprising:
  generating data indicative of a plurality of tabletop motion profiles, wherein the motion profiles correspond to algorithms from a group consisting of: a sinusoidal harmonic axial algorithm; a profile shaped axial algorithm; a time compensated band pass filtered axial algorithm; a sinusoidal harmonic perfusion algorithm; and a filtered perfusion axial;
  storing the plurality of tabletop motion profiles in storage accessible to a subject support controller configured to control a tabletop of a subject support during a scan;
  selecting and employing one of the motion profiles based on a type of a scan for a scan protocol selected for scanning the subject.

20. An imaging system, comprising:
  a subject support configured to carry a subject being imaged in an examination region of the imaging system; and
  a subject support controller that controls horizontal motion of the subject support based on a sinusoidal motion profile with the following position, velocity and acceleration profiles:

$$s(t) = A\left\{\frac{t}{T} - \frac{1}{2\pi}\sin\left(2\pi\frac{t}{T}\right)\right\};$$

$$v(t) = \frac{A}{T}\left\{1 - \cos\left(2\pi\frac{t}{T}\right)\right\}; \text{ and}$$

$$a(t) = \frac{2\pi A}{T^2}\sin\left(2\pi\frac{t}{T}\right),$$

wherein s represents a real-time subject support position, v represents a real-time subject support velocity, α represents a real-time subject support acceleration, A represents a single step subject support move distance, T represents a subject support move period, and t represents a time index.

21. An imaging system, comprising:
  a subject support configured to carry a subject being imaged in an examination region of the imaging system; and
  a subject support controller that controls horizontal motion of the subject support based on a sinusoidal motion profile with the following subject support position, velocity and acceleration profiles:

$$s(t) = \frac{A}{2}\left(1 - \cos\left(\pi\frac{t}{T}\right)\right);$$

$$v(t) = \frac{A}{2} \cdot \frac{\pi}{T}\sin\left(\pi\frac{t}{T}\right)$$

and $$a(t) = \frac{A}{2} \cdot \left(\frac{\pi}{T}\right)^2 \cos\left(\pi\frac{t}{T}\right),$$

wherein s represents a real-time subject support position, v represents a real-time subject support velocity, α represents a real-time subject support acceleration, A represents cyclic end-to-end subject support move distance, T represents end-to-end subject support move time, and t represents a time index.

* * * * *